United States Patent
Dunbar et al.

(10) Patent No.: US 10,434,278 B2
(45) Date of Patent: Oct. 8, 2019

(54) SYSTEM FOR IMAGE GUIDED PROCEDURE

(71) Applicant: eZono AG, Jena (DE)

(72) Inventors: Allan Dunbar, Jena (DE); Eliseo Sobrino, Jena (DE)

(73) Assignee: EZONO AG, Jena (DE)

( * ) Notice: Subject to any disclaimer, the term of this patent is extended or adjusted under 35 U.S.C. 154(b) by 381 days.

(21) Appl. No.: 14/759,176

(22) PCT Filed: Mar. 5, 2014

(86) PCT No.: PCT/EP2014/054276
§ 371 (c)(1),
(2) Date: Jul. 2, 2015

(87) PCT Pub. No.: WO2014/135592
PCT Pub. Date: Sep. 12, 2014

(65) Prior Publication Data
US 2015/0359991 A1     Dec. 17, 2015

(30) Foreign Application Priority Data

Mar. 5, 2013  (GB) .................................. 1303917.7

(51) Int. Cl.
*A61B 8/08*      (2006.01)
*A61B 8/00*      (2006.01)
(Continued)

(52) U.S. Cl.
CPC ........... *A61M 19/00* (2013.01); *A61B 5/0538* (2013.01); *A61B 5/062* (2013.01); *A61B 5/7425* (2013.01);
(Continued)

(58) Field of Classification Search
CPC ....... A61B 5/061; A61B 5/066; A61B 8/4254; A61B 34/20; A61B 2034/107; A61B 2034/2065
See application file for complete search history.

(56) References Cited

U.S. PATENT DOCUMENTS 4,317,078 A    2/1982  Weed
4,508,119 A    4/1985  Tukamoto
(Continued)

FOREIGN PATENT DOCUMENTS

AT         455499         2/2010
AT         492214         1/2011
(Continued)

OTHER PUBLICATIONS

Stolowitz Ford Cowger LLP, Listing of Related Cases; Portland, OR; Aug. 19, 2015; 1 page.
(Continued)

*Primary Examiner* — Baisakhi Roy
*Assistant Examiner* — Jason M Ip
(74) *Attorney, Agent, or Firm* — Schwabe Williamson & Wyatt, PC

(57) ABSTRACT

A system for supplementing ultrasound image needle guidance with magnetically detected needle position and tissue impedance measurements. The system comprises an ultrasound imaging system with the ultrasound probe being provided with a magnetometric detector for detecting the position of a magnetized needle, cannula, catheter or other tissue-penetrating tool. The tissue penetrating tool is provided with an electrode at or near its tip which is connected to a power source and impedance meter, the impedance measuring circuit being completed by use of a skin electrode or second electrode on the tool so that the electrical impedance of the patient's tissue can be measured. The measured (Continued)

impedance values and the magnetically detected position of the tool are superimposed on the ultrasound image so that the clinician can easily confirm the needle position in relation to the imaged anatomy. The impedance values may be color-coded or charted alongside or superimposed on the position or track of the needle as displayed on the ultrasound image.

17 Claims, 4 Drawing Sheets

(51) Int. Cl.
    *A61B 5/053*     (2006.01)
    *A61B 17/34*     (2006.01)
    *A61B 5/06*     (2006.01)
    *A61B 34/20*     (2016.01)
    *A61B 5/00*     (2006.01)
    *A61M 19/00*     (2006.01)
    *A61B 90/00*     (2016.01)

(52) U.S. Cl.
    CPC .......... *A61B 8/0841* (2013.01); *A61B 8/4254* (2013.01); *A61B 17/3403* (2013.01); *A61B 34/20* (2016.02); *A61B 2017/3413* (2013.01); *A61B 2034/2051* (2016.02); *A61B 2034/2072* (2016.02); *A61B 2034/2074* (2016.02); *A61B 2090/364* (2016.02); *A61B 2090/378* (2016.02)

(56) References Cited

U.S. PATENT DOCUMENTS

| | | | |
|---|---|---|---|
| 5,042,486 A | | 4/1991 | Pfeiler |
| 5,055,813 A | | 10/1991 | Johnson |
| 5,425,382 A | | 6/1995 | Golden |
| 5,622,169 A | | 4/1997 | Golden |
| 5,744,953 A | | 4/1998 | Hansen |
| 5,767,669 A | | 6/1998 | Hansen |
| 5,831,260 A | | 11/1998 | Hansen |
| 5,833,608 A | | 11/1998 | Acker |
| 5,879,297 A | | 3/1999 | Haynor |
| 5,902,238 A | | 5/1999 | Golden |
| 5,941,889 A | | 8/1999 | Cermak |
| 5,944,023 A | | 8/1999 | Johnson |
| 5,953,683 A | | 9/1999 | Hansen |
| 6,052,610 A | | 4/2000 | Koch |
| 6,073,043 A | | 6/2000 | Schneider |
| 6,101,410 A | * | 8/2000 | Panescu ............... A61B 5/0422 340/2.26 |
| 6,172,499 B1 | | 1/2001 | Ashe |
| 6,198,956 B1 | | 3/2001 | Dunne |
| 6,216,028 B1 | | 4/2001 | Haynor |
| 6,233,476 B1 | | 5/2001 | Strommer |
| 6,246,231 B1 | | 6/2001 | Ashe |
| 6,246,898 B1 | | 6/2001 | Vesely |
| 6,248,074 B1 | | 6/2001 | Ohno |
| 6,263,230 B1 | | 7/2001 | Haynor |
| 6,266,551 B1 | | 7/2001 | Osadchy |
| 6,310,532 B1 | | 10/2001 | Santa Cruz |
| 6,315,724 B1 | | 11/2001 | Berman |
| 6,336,899 B1 | | 1/2002 | Yamazaki |
| 6,361,499 B1 | | 3/2002 | Bates |
| 6,368,280 B1 | | 4/2002 | Cermak |
| 6,379,307 B1 | | 4/2002 | Filly |
| 6,427,079 B1 | | 7/2002 | Schneider |
| 6,438,401 B1 | | 8/2002 | Cheng |
| 6,453,190 B1 | | 9/2002 | Acker |
| 6,528,991 B2 | | 3/2003 | Ashe |
| 6,542,766 B2 | | 4/2003 | Hall |
| 6,546,279 B1 | | 4/2003 | Bova |
| 6,587,709 B2 | | 7/2003 | Soif |
| 6,626,832 B1 | | 9/2003 | Paltieli |
| 6,669,635 B2 | | 12/2003 | Kessman |
| 6,678,552 B2 | | 1/2004 | Pearlman |
| 6,690,159 B2 | | 2/2004 | Burreson |
| 6,690,963 B2 | | 2/2004 | Ben-Haim |
| 6,716,166 B2 | | 4/2004 | Govari |
| 6,733,458 B1 | | 5/2004 | Steins |
| 6,754,596 B2 | | 6/2004 | Ashe |
| 6,774,624 B2 | | 8/2004 | Anderson |
| 6,784,660 B2 | | 8/2004 | Ashe |
| 6,785,571 B2 | | 8/2004 | Glossop |
| 6,788,967 B2 | | 9/2004 | Ben-Haim |
| 6,813,512 B2 | | 11/2004 | Aldefeld |
| 6,834,201 B2 | | 12/2004 | Gillies |
| 6,856,823 B2 | | 2/2005 | Ashe |
| 6,895,267 B2 | | 5/2005 | Panescu |
| 6,954,128 B2 | | 10/2005 | Humphries |
| 6,980,921 B2 | | 12/2005 | Anderson |
| 7,020,512 B2 | | 3/2006 | Ritter |
| 7,048,745 B2 | | 5/2006 | Tierney |
| 7,090,639 B2 | | 8/2006 | Govari |
| 7,197,354 B2 | | 3/2007 | Sobe |
| 7,215,990 B2 | | 5/2007 | Feussner |
| 7,274,325 B2 | | 9/2007 | Fattah |
| 7,275,008 B2 | | 9/2007 | Plyvanainen |
| 7,324,915 B2 | | 1/2008 | Altmann |
| 7,351,205 B2 | | 4/2008 | Szczech |
| 7,373,271 B1 | | 5/2008 | Schneider |
| 7,386,339 B2 | | 6/2008 | Strommer |
| 7,471,202 B2 | | 12/2008 | Anderson |
| 7,505,810 B2 | | 3/2009 | Harlev |
| 7,517,318 B2 | | 4/2009 | Altmann |
| 7,524,320 B2 | | 4/2009 | Tierney |
| 7,551,953 B2 | | 6/2009 | Lardo |
| 7,555,330 B2 | | 6/2009 | Gilboa |
| 7,558,616 B2 | | 7/2009 | Govari |
| 7,561,051 B1 | | 7/2009 | Kynor |
| 7,573,258 B2 | | 8/2009 | Anderson |
| 7,588,541 B2 | | 9/2009 | Floyd |
| 7,603,155 B2 | | 10/2009 | Jensen |
| 7,603,160 B2 | | 10/2009 | Suzuki |
| 7,610,078 B2 | | 10/2009 | Willis |
| 7,618,374 B2 | | 11/2009 | Barnes |
| 7,636,595 B2 | | 12/2009 | Marquart |
| 7,652,259 B2 | | 1/2010 | Kimchy |
| 7,657,298 B2 | | 2/2010 | Moctezuma de la Barrera |
| 7,660,623 B2 | | 2/2010 | Hunter |
| 7,668,583 B2 | | 2/2010 | Fegert |
| 7,671,887 B2 | | 3/2010 | Pescatore |
| 7,697,973 B2 | | 4/2010 | Strommer |
| 7,706,860 B2 | | 4/2010 | McGee |
| 7,722,565 B2 | | 5/2010 | Wood |
| 7,749,168 B2 | | 7/2010 | Maschke |
| 7,769,427 B2 | | 8/2010 | Shachar |
| 7,797,032 B2 | | 9/2010 | Martinelli |
| 7,806,824 B2 | | 10/2010 | Ohtake |
| 7,809,421 B1 | | 10/2010 | Govari |
| 7,819,810 B2 | | 10/2010 | Stringer |
| 7,822,464 B2 | | 10/2010 | Maschke |
| 7,831,096 B2 | | 11/2010 | Williamson, Jr. |
| 7,835,785 B2 | | 11/2010 | Scully |
| 7,840,251 B2 | | 11/2010 | Glossop |
| 7,840,253 B2 | | 11/2010 | Tremblay |
| 7,840,256 B2 | | 11/2010 | Lakin |
| 7,873,401 B2 | | 1/2011 | Shachar |
| 7,881,769 B2 | | 1/2011 | Sobe |
| 7,907,989 B2 | | 3/2011 | Borgert |
| 7,909,815 B2 | | 3/2011 | Whitmore, III |
| 7,926,776 B2 | | 4/2011 | Cermak |
| 7,945,309 B2 | | 5/2011 | Govari |
| 7,962,196 B2 | | 6/2011 | Tuma |
| 7,966,057 B2 | | 6/2011 | Macaulay |
| 7,971,341 B2 | | 7/2011 | Dukesherer |
| 7,974,680 B2 | | 7/2011 | Govari |
| 7,996,059 B2 | | 8/2011 | Porath |
| 8,023,712 B2 | | 9/2011 | Ikuma |
| 8,027,714 B2 | | 9/2011 | Shachar |
| 8,041,411 B2 | | 10/2011 | Camus |
| 8,041,412 B2 | | 10/2011 | Glossop |
| 8,041,413 B2 | | 10/2011 | Barbagli |
| 8,049,503 B2 | | 11/2011 | Kimura |

(56) References Cited

U.S. PATENT DOCUMENTS

| | | |
|---|---|---|
| 8,060,184 B2 | 11/2011 | Hastings |
| 8,064,985 B2 | 11/2011 | Peterson |
| 8,068,897 B1 | 11/2011 | Gazdzinski |
| 8,073,529 B2 | 12/2011 | Cermak |
| 8,079,982 B1* | 12/2011 | Ponzi .................. A61B 18/1492 604/115 |
| 8,082,022 B2 | 12/2011 | Moctezuma de la Barrera |
| 8,086,298 B2 | 12/2011 | Whitmore, III |
| 8,088,070 B2 | 1/2012 | Pelissier |
| 8,090,168 B2 | 1/2012 | Washburn |
| 8,106,905 B2 | 1/2012 | Markowitz |
| 8,147,408 B2 | 4/2012 | Bunce |
| 8,162,821 B2 | 4/2012 | Kawano |
| 8,175,680 B2 | 5/2012 | Panescu |
| 8,216,149 B2 | 7/2012 | Oonuki |
| 8,226,562 B2 | 7/2012 | Pelissier |
| 8,228,028 B2 | 7/2012 | Schneider |
| 8,506,493 B2 | 8/2013 | Ostrovsky |
| 2002/0103431 A1* | 8/2002 | Toker ...................... A61B 6/04 600/436 |
| 2003/0036695 A1 | 2/2003 | Govari |
| 2003/0220557 A1 | 11/2003 | Cleary |
| 2004/0047044 A1 | 3/2004 | Dalton |
| 2004/0051610 A1 | 3/2004 | Sajan |
| 2004/0106869 A1 | 6/2004 | Tepper |
| 2004/0147920 A1 | 7/2004 | Keidar |
| 2004/0171934 A1 | 9/2004 | Khan |
| 2005/0020919 A1 | 1/2005 | Stringer |
| 2005/0033315 A1 | 2/2005 | Hankins |
| 2005/0101876 A1 | 5/2005 | Pearlman |
| 2005/0107870 A1 | 5/2005 | Wang |
| 2005/0137659 A1* | 6/2005 | Garabedian .......... A61B 18/148 607/96 |
| 2005/0143648 A1 | 6/2005 | Minai |
| 2005/0197569 A1 | 9/2005 | McCombs |
| 2006/0061354 A1 | 3/2006 | Wallance |
| 2006/0072843 A1 | 4/2006 | Johnston |
| 2006/0241397 A1 | 10/2006 | Govari |
| 2006/0247600 A1 | 11/2006 | Yeung |
| 2006/0253107 A1 | 11/2006 | Hashimshony |
| 2007/0016013 A1 | 1/2007 | Camus |
| 2007/0027390 A1 | 2/2007 | Maschke |
| 2007/0049846 A1 | 3/2007 | Bown |
| 2007/0055468 A1 | 3/2007 | Plyvanainen |
| 2007/0163367 A1 | 7/2007 | Sherman |
| 2007/0167801 A1 | 7/2007 | Webler |
| 2007/0185398 A1 | 8/2007 | Kimura |
| 2007/0276240 A1 | 11/2007 | Rosner |
| 2008/0027475 A1 | 1/2008 | Grundmann |
| 2008/0033286 A1 | 2/2008 | Whitmore |
| 2008/0036580 A1 | 2/2008 | Breed |
| 2008/0071172 A1 | 3/2008 | Bruck |
| 2008/0094057 A1 | 4/2008 | Ashe |
| 2008/0134727 A1 | 6/2008 | May |
| 2008/0146939 A1 | 6/2008 | McMorrow |
| 2008/0183071 A1 | 7/2008 | Strommer |
| 2008/0228195 A1 | 9/2008 | von Jako |
| 2008/0249395 A1 | 10/2008 | Shachar |
| 2008/0262338 A1 | 10/2008 | Paitel |
| 2009/0070063 A1 | 3/2009 | Edelstein |
| 2009/0105581 A1 | 4/2009 | Widenhorn |
| 2009/0105584 A1 | 4/2009 | Jones |
| 2009/0105779 A1 | 4/2009 | Moore |
| 2009/0156926 A1 | 6/2009 | Messerly |
| 2009/0184825 A1 | 7/2009 | Anderson |
| 2009/0203989 A1 | 8/2009 | Burnside |
| 2009/0228019 A1 | 9/2009 | Gross |
| 2009/0275833 A1 | 11/2009 | Ikeda |
| 2009/0287443 A1 | 11/2009 | Jascob |
| 2009/0299142 A1 | 12/2009 | Uchiyama |
| 2009/0299176 A1 | 12/2009 | Gleich |
| 2009/0312629 A1 | 12/2009 | Razzaque |
| 2009/0322323 A1 | 12/2009 | Brazdeikis |
| 2009/0326323 A1 | 12/2009 | Uchiyama |
| 2010/0036241 A1 | 2/2010 | Mayse |
| 2010/0049033 A1 | 2/2010 | Kawano |
| 2010/0049050 A1 | 2/2010 | Pelissier |
| 2010/0079158 A1 | 4/2010 | Bar-Tal |
| 2010/0121189 A1 | 5/2010 | Ma |
| 2010/0121190 A1 | 5/2010 | Pagoulatos |
| 2010/0137705 A1 | 6/2010 | Jensen |
| 2010/0156399 A1 | 6/2010 | Chiba |
| 2010/0174176 A1 | 7/2010 | Nagel |
| 2010/0191101 A1 | 7/2010 | Lichtenstein |
| 2010/0228119 A1 | 9/2010 | Brennan |
| 2010/0249576 A1 | 9/2010 | Askarinya |
| 2010/0268072 A1 | 10/2010 | Hall |
| 2010/0286517 A1* | 11/2010 | Kamen .............. A61B 10/0241 600/438 |
| 2010/0312113 A1 | 12/2010 | Ogasawara |
| 2011/0021903 A1 | 1/2011 | Strommer |
| 2011/0028848 A1 | 2/2011 | Shaquer |
| 2011/0034806 A1 | 2/2011 | Hartov |
| 2011/0054293 A1 | 3/2011 | Markowitz |
| 2011/0060185 A1 | 3/2011 | Ikuma |
| 2011/0081063 A1 | 4/2011 | Leroy |
| 2011/0082366 A1 | 4/2011 | Scully |
| 2011/0118590 A1 | 5/2011 | Zhang |
| 2011/0137152 A1 | 6/2011 | Li |
| 2011/0137156 A1 | 6/2011 | Razzaque |
| 2011/0144476 A1 | 6/2011 | Jolesz |
| 2011/0144524 A1 | 6/2011 | Fish |
| 2011/0184690 A1 | 7/2011 | Iida |
| 2011/0224537 A1 | 9/2011 | Brunner |
| 2011/0230757 A1 | 9/2011 | Elgort |
| 2011/0237945 A1 | 9/2011 | Foroughi |
| 2011/0251607 A1 | 10/2011 | Kruecker |
| 2011/0282188 A1 | 11/2011 | Burnside |
| 2011/0295108 A1 | 12/2011 | Cox |
| 2011/0295110 A1 | 12/2011 | Manzke |
| 2012/0016316 A1 | 1/2012 | Zhuang |
| 2012/0071752 A1 | 3/2012 | Sewell |
| 2012/0108950 A1 | 5/2012 | He |
| 2012/0123243 A1 | 5/2012 | Hastings |
| 2012/0130229 A1 | 5/2012 | Zellers |
| 2012/0130230 A1 | 5/2012 | Eichler |
| 2012/0136251 A1 | 5/2012 | Kim |
| 2012/0143055 A1 | 6/2012 | Ng |
| 2012/0150022 A1 | 6/2012 | Bar-Tal |
| 2012/0197108 A1 | 8/2012 | Hartmann |
| 2012/0232380 A1 | 9/2012 | Pelissier |
| 2012/0259209 A1 | 10/2012 | Harhen |
| 2013/0225986 A1 | 8/2013 | Eggers |
| 2013/0296691 A1 | 11/2013 | Ashe |
| 2014/0002063 A1 | 1/2014 | Ashe |
| 2014/0046261 A1 | 2/2014 | Newman |
| 2014/0058221 A1 | 2/2014 | Old |
| 2014/0107475 A1 | 4/2014 | Cox |
| 2014/0228670 A1 | 8/2014 | Justis |
| 2014/0253270 A1 | 9/2014 | Nicholls |
| 2014/0257080 A1 | 9/2014 | Dunbar |
| 2014/0257104 A1 | 9/2014 | Dunbar |
| 2014/0257746 A1 | 9/2014 | Dunbar |
| 2015/0080710 A1 | 3/2015 | Henkel |
| 2017/0079549 A1 | 2/2017 | Henkel |
| 2017/0079550 A1 | 3/2017 | Henkel |
| 2017/0079551 A1 | 3/2017 | Henkel |

FOREIGN PATENT DOCUMENTS

| | | |
|---|---|---|
| CA | 2 647 432 A1 | 10/2007 |
| CA | 2659586 A1 | 12/2007 |
| CN | 102860841 A | 1/2013 |
| DE | 10 2008 013 611 A1 | 9/2009 |
| DE | 10 2010 046 948 A1 | 12/2011 |
| EP | 0 488 987 A1 | 6/1992 |
| EP | 0 747 016 A1 | 12/1996 |
| EP | 0 928 976 A2 | 7/1999 |
| EP | 1 212 001 A2 | 6/2002 |
| EP | 1 377 335 A2 | 1/2004 |
| EP | 1 504 713 A1 | 2/2005 |
| EP | 1 715 788 A2 | 11/2006 |
| EP | 1 727 478 A | 12/2006 |
| EP | 1 804 079 A2 | 7/2007 |

(56) References Cited

FOREIGN PATENT DOCUMENTS

| | | |
|---|---|---|
| EP | 1 898 775 A2 | 3/2008 |
| EP | 1 913 875 A1 | 4/2008 |
| GB | 2 445 699 A | 7/2008 |
| JP | H10512462 | 2/1998 |
| JP | 2000185041 | 7/2000 |
| JP | 2003334191 | 11/2003 |
| JP | 2005-312577 A | 11/2005 |
| JP | 2007203039 | 8/2007 |
| WO | 1996/005768 A1 | 2/1996 |
| WO | 9612439 | 5/1996 |
| WO | 2000/063658 A2 | 10/2000 |
| WO | 2002/000093 A2 | 1/2002 |
| WO | 2006/078677 A2 | 7/2006 |
| WO | 2006/078678 A2 | 7/2006 |
| WO | 2006/124192 A2 | 11/2006 |
| WO | 2007/025081 A2 | 3/2007 |
| WO | 2008/035271 A2 | 3/2008 |
| WO | 2008/086832 A1 | 7/2008 |
| WO | 2009/070616 A2 | 6/2009 |
| WO | 2009/089280 A1 | 7/2009 |
| WO | 2010/111435 A1 | 9/2010 |
| WO | 2010/132985 A1 | 11/2010 |
| WO | 2011/043874 A1 | 4/2011 |
| WO | 2011/043875 A1 | 4/2011 |
| WO | 2011/044273 A2 | 4/2011 |
| WO | 2011/085034 A1 | 7/2011 |
| WO | 2011082451 | 7/2011 |
| WO | 2011/095924 A1 | 8/2011 |
| WO | 2011/098926 A1 | 8/2011 |
| WO | 2011/109249 A1 | 9/2011 |
| WO | 2011/114259 A1 | 9/2011 |
| WO | 2011/123661 A1 | 10/2011 |
| WO | 2011/127191 A1 | 10/2011 |
| WO | 2011/150376 A1 | 12/2011 |
| WO | 2012/025854 A1 | 3/2012 |
| WO | 2012/040077 A1 | 3/2012 |
| WO | 2012058461 | 5/2012 |
| WO | 2012/098483 A1 | 7/2012 |
| WO | 2013/034175 A1 | 3/2013 |
| WO | 2011150376 | 4/2013 |
| WO | 2014/135592 A1 | 9/2014 |

OTHER PUBLICATIONS

European Patent Office International Search Report for PCT/EP2011/065420; dated Aug. 20, 2012; 5 pages.

Placidi, Giuseppe, et al.; "Review on Patents about Magnetic Localisation Systems for in vito Catheterizations"; INFM c/o Department of Health Sciences, University of L'Aquila, Via Vetoio Coppito 2, 67100 L'Aquila, Italy; Recent Patents on Biomedical Engineering 2009, 2, 58-64; Received: Dec. 24, 2008; Accepted: Jan. 9, 2009; Revised: Jan. 12, 2009; 8 pages.

Dorveaux et al.; "On-the-field Calibration of an Array of Sensors"; 2010 American Control Conference; Jun. 30-Jul. 2, 2010; Baltimore, MD; USA; 8 pages.

* cited by examiner

Fig. 3(A)

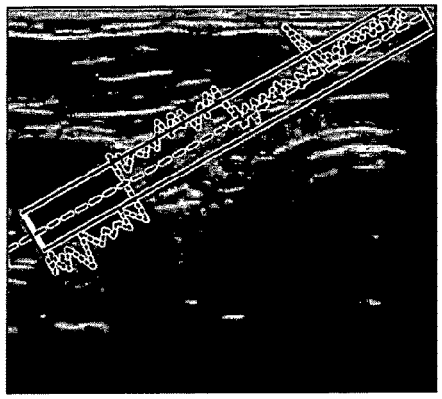

Needle Path/trajectory     ---------
Needle position
Measured Impedance value

Above: Raw impedance values charted at needle tip over its path on ultrasound image

Fig. 3(B)

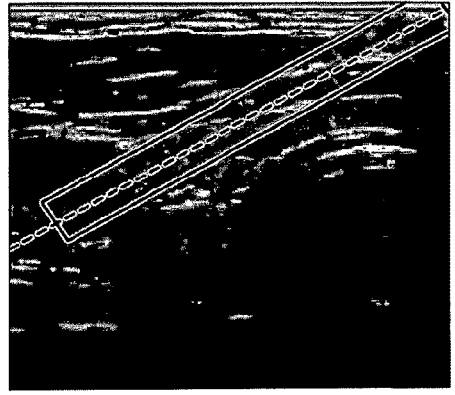

Needle Path/trajectory     ---------
Needle position
Measured Impedance value (using heat based colour scheme)   Low    High
Above: Raw impedance values colour coded at needle tip over its path on ultrasound image according to standard colour schemes e.g. heat, topographic, etc.

Fig. 3(C)

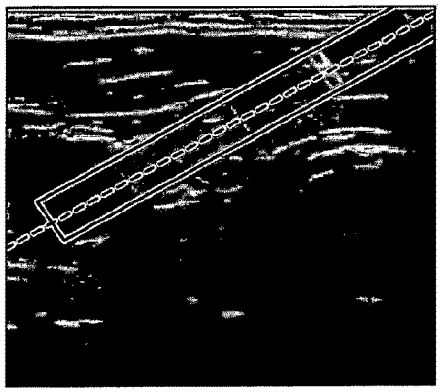

Needle Path/trajectory     ---------
Needle position
Measured Impedance value (colours correspond to identified tissue type uses standard medical text book colouring)
Above: Raw impedance values converted to tissue type and colour coded at needle tip over its path on the ultrasound image according to standard medical anatomy text book colour coding i.e. nerves are yellow, arteries are red

Fig. 3(D)

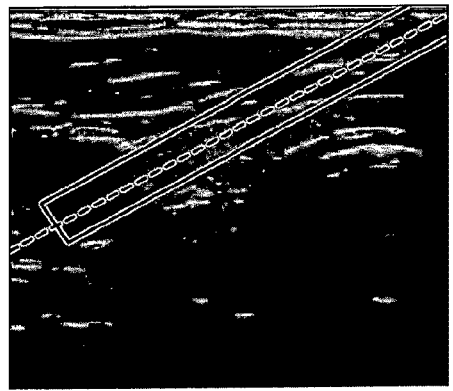

Needle Path/trajectory     ---------
Needle position
Measured Impedance value (colour shown only at the needle tip position)
Above: Raw impedance or converted values colour coded only at needle tip position on ultrasound image Needle Path/trajectory   ----------
Needle position          ——————
Measured Impedance value ——————

(chain dot lines map impedance traces to tip position)

Above: Raw impedance values charted along x and y axis off the ultrasound image in line with needle tip position on ultrasound image

SYSTEM FOR IMAGE GUIDED PROCEDURE

The present invention relates generally to the field of medical devices and in particular to a system for improving image guided procedures such as needle or catheterisation procedures.

There are numerous medical procedures that involve the insertion of a medical tool or instrument, such as a needle, cannula, catheter or stylet, into a subject's body, e.g. minimally-invasive surgical procedures, regional anaesthesia, detection of bio-electrical signals, electrical stimulation for diagnosis or treatment, vascular access, fine needle aspiration, musculoskeletal injections and so on. In such procedures it is generally necessary to guide the medical tool properly to the desired position in the subject's body and it can also be beneficial to monitor or track the medical tool position to ensure that it remains at the desired location. In general it is very difficult for the user to determine the exact position of the tip of the medical tool and thus to be sure whether it is in the desired place, for example adjacent a nerve, or whether it has undesirably penetrated something else, for example a blood vessel.

It has been proposed to use x-ray techniques for needle guidance by providing the clinician with an x-ray image of the needle in the body. However in view of the risks associated with exposure to electromagnetic radiation, it is not possible to provide a continuous guidance during insertion of the medical tool and so a series of snapshots are relied upon, which does not give optimal guidance.

More recently the use of ultrasound imaging to guide needle and catheterisation procedures has been proposed. Ultrasound imaging is advantageous compared to x-ray techniques because of the lack of exposure to electromagnetic radiation, and ultrasound probes are easily manipulatable to image many different parts of the body. However ultrasound imaging has two main challenges: firstly that the interpretation of ultrasound images is rather difficult, and secondly that needles do not show-up particularly reliably or visibly in the ultrasound image.

In more detail, ultrasound images provide only grayscale cross-sectional planes at a range of angles through the body depending on how the ultrasound transducer is applied. Traditional teaching of anatomy to doctors is in only six standard planes of the body and anatomic parts are typically coloured in diagrams to identify nerves, arteries, muscle, tissue etc. Therefore identifying anatomy clearly in ultrasound images requires a significant amount of learning and experience. This is a problem in extending the use of ultrasound imaging to the increasing variety of minimally-invasive surgical techniques where it is desirable if the practitioners performing the technique can do the ultrasound imaging themselves, rather than have to rely on a skilled radiologist. Further, for certain parts of the body ultrasound images intrinsically do not show the relevant anatomy very well. For example in the case of supra-clavicular nerve blocks involving the injection of anaesthetic around a nerve, studies have shown that in up to 20% of patients' blood vessels are found amongst the nerve bundles. In an ultrasound image both nerves and blood vessels are represented as black disks surrounded by white circles and so differentiation can be difficult meaning that it is difficult for the clinician to know exactly where the needle tip is. Similarly, when performing spinal injections, e.g. epidurals, ultrasound images show only muscle and bone and cannot penetrate bone, so it cannot see beyond the dura (the outermost of the three layers of membranes surrounding the spinal cord). Further the surface of the bone is only seen at a narrow range of angles. Therefore ultrasound image quality is very poor around the spine. However in the epidural anaesthetic injection, it is necessary for the needle to inject into the epidural space, but not to advance further and puncture the dura. On the other hand for a spinal anaesthetic, penetration of the dura is required to allow injection into the subarachnoid space. Ultrasound imaging is not capable of determining the difference between these two cases.

As to the problem of needle visibility, the ultrasound image acquisition plane is thin—of the order of 1 mm thick, and so if the needle is out of that plane it will not be imaged. Further, even when the needle is in the imaging plane, because the echogenicity of standard needles is poor at high angles of incidence, the needle may not be particularly visible. It has been proposed to produce echogenic needles which make the needle more visible to ultrasound imaging devices. However these only help when the needle is well-aligned with the imaging plane. Similarly techniques for image processing and ultrasound beam steering help only when the needle is well-aligned with the imaging plane and do not work well for angles of incidence greater than 45 degrees.

Various needle tracking technologies have been proposed based either on a needle guide fitted to an ultrasound probe, e.g. U.S. Pat. No. 6,690,159 or WO-A-2012/040077, or based on the transmission and reception of electromagnetic information, e.g. US-A-2007-027390) but have functional and accuracy limitations which means that the needle tip position is not exactly known in every clinical circumstance. Typical accuracies are of the order of 2 mm, which can mean the difference between the needle tip being inside or outside a nerve. Further they often require the use of heavily modified or new equipment which is unwelcome to clinicians and to institutions with relatively rigid purchasing regimes.

Most often, therefore, practitioners rely on their skill and experience to judge what type of tissue is being penetrated as the needle or other medical tool is inserted. They may rely on sound, the touch and feel of the physical resistance to the medical tool and sudden changes in resistance, and changes in resistance to the injection of air or fluids. Developing this level of skill and experience, though, is time-consuming and difficult and as there is an anatomical variation from patient to patient, the procedures inevitably entail some risks.

In summary, although ultrasound guidance has improved some needling procedures, there are still significant difficulties and it cannot be used for many procedures. This is a major barrier to its widespread use, particularly its use by practitioners who are not medical imaging specialists, such as anaesthetists, surgeons, pathologists, emergency physicians etc.

Accordingly, the present invention provides an improved system for image-guided procedures which combines imaging of the subject's internal anatomy with tracking of the tissue-penetrating medical tool and display of the tracked position on the displayed anatomical image, together with making available to the user a third source of information based on a measurement of a bio-electrical property of the tissue being penetrated. Advantageously the measured electrical property comprises the electrical impedance, and preferably it is displayed on the same display as the anatomical image, either overlaid on the image or alongside it. For example the impedance value may be displayed as a chart or colour coding along the displayed needle position or path on the anatomical image.

The imaging may be ultrasound imaging—e.g. freehand ultrasound, fluorsoscopy, X-ray imaging, nuclear imaging, magnetic resonance imaging, thermoacoustic imaging, thermography. The tool may be tracked magnetically, electromagnetically, optically or by ultrasound.

Interest and experimentation in the electrical properties of tissue began in the late 1800s. It is now well known that different tissue types have different electrical impedance/frequency response curves. It has been proposed, for example in WO2009/019707 to use a hand-held electrical device provided with a needle carrying two electrodes to measure the impedance of tissue inside a body but this special device gives only one-dimensional information about the tissue at the tip of the needle with no relative anatomical information. A technique known as electrical impedance tomography (EIT) has also been proposed which uses an array of electrodes on the surface of the body to reconstruct an impedance distribution within the body. This technique requires multiple electrodes, and the analysis of the signals to reconstruct the impedance distribution is highly complex. The spatial resolution of the technique is limited and so the anatomy is not clear in the images produced. Further, typically only a two-dimensional image is obtained of an area parallel to the body's surface and no information about depth is obtained. The images obtained also change significantly with the frequency at which impedance is measured, and introducing metal surgical devices into the body while acquiring image data would change the impedance fields being measured and change the images. Thus the main focus of EIT is on non-interventional medical applications, such as diagnostics and in fact there is still some doubt over its diagnostic capability. At present it is best seen as an additional imaging modality for use in breast cancer diagnosis.

The present invention combines measurement of a bio-electrical property of the tissue in an interventional surgical procedure with anatomical imaging and tool tracking to overcome the disadvantages above and provide the clinician with an enhanced picture of the interventional procedure.

In more detail the invention provides a system comprising: a medical imaging system for imaging a subject's internal anatomy; a tissue-penetrating medical tool having an insertion end for insertion into the body of the subject; a position detection system for detecting the position of the tissue-penetrating medical tool in the body of the subject; a first electrode provided at the insertion end, i.e. towards the tip or on the tip, of the tissue-penetrating medical tool electrically-connected to an electrical system for measuring a bio-electrical property of the subject; and a processor and display for analysing displaying the anatomical image from the medical imaging system and adapted to display on the anatomical image the position of the tissue-penetrating medical tool as detected by the position detection system. The invention also provides a corresponding method comprising the steps of: imaging a subject's internal anatomy while inserting an insertion end of a tissue-penetrating medical tool into the body of the subject; detecting the position of the tissue-penetrating medical tool in the body of the subject; using a first electrode provided at the insertion end, i.e. towards the tip or on the tip, of the tissue-penetrating medical tool to measure a bio-electrical property of the subject; and displaying an image showing the anatomy of the subject and the detected position of the tissue-penetrating medical tool.

The medical imaging system may be one of ultrasound, fluorsoscopy, X-ray, nuclear imaging, magnetic resonance imaging, thermoacoustic imaging or thermography, more preferably the medical imaging system is freehand ultrasound. The position detection system is preferably a magnetic position detection system, an optical tracking system, an electromagnetic tracking system, an ultrasonic tracking system, an x-ray or a fluoroscopic tracking system. The magnetic position detection system may comprise a magnetised tool and magnetometric detector. The magnetometric detector may be combined with part of the imaging system, such as an ultrasound probe as described below. Alternatively, particularly with electromagnetic tracking, sensors, e.g. sensor coils may be provided on the tool to detect an applied varying magnetic field and transmit an induced electrical signal to a system for determining the position.

Preferably at least one second electrode is provided in contact with the subject, this may be in contact with the skin or on the tissue-penetrating medical tool or on another tissue-penetrating medical tool. The bio-electrical property may electrical impedance, e.g. resistance, impedance or capacitance or a combination thereof.

The electrical system may be connected to the processor and display to display the measured bio-electrical property with the anatomical image on the display. The processor and display may be adapted to display a chart of the measured bio-electrical property over the display of the position of the tissue-penetrating medical tool in the anatomical image. The processor and display may be adapted to display the measured bio-electrical property by setting a display attribute in the anatomical image according to the value of the measured bio-electrical property. The processor and display may be adapted to set display attributes along the displayed position of the tissue-penetrating medical tool in the anatomical image according to the value of the measured bio-electrical property. The processor and display may be adapted to set display attributes at the displayed position of the insertion end of the tissue-penetrating medical tool in the anatomical image according to the value of the measured bio-electrical property. The display attribute set may be the colour or grayscale value. The processor may be adapted to determine a tissue type from the value of the measured bio-electrical property and to display the anatomical image with areas colour coded according to tissue type using standard medical anatomy colour coding.

The processor and display may be adapted to display a chart of the measured bio-electrical property alongside the anatomical image. The processor and display may be adapted to display the change of measured bio-electrical property as the tissue-penetrating medical tool is moved through the subject's body.

The tissue-penetrating medical tool may be a needle. The first electrode may be provided at the tip of the tissue-penetrating medical tool. A second electrode may be provided on a stimulating catheter for insertion through the tissue-penetrating medical tool. A second electrode may be provided on a needle of different gauge for insertion into the tissue-penetrating medical tool. A second electrode may be provided on a stylet for insertion into the tissue-penetrating medical tool. A second electrode is provided on the insertion end of the tissue-penetrating medical tool spaced from the first electrode.

More specifically one advantageous embodiment of the invention provides a system comprising: an ultrasound transducer for transmitting ultrasound into a subject's body and receiving ultrasound echoes from the body; a tissue-penetrating medical or surgical tool or instrument having an insertion end for insertion into the body of the subject; a position detection system for detecting the position of the tissue-penetrating medical tool in the body of the subject; a first electrode provided at the insertion end of the tissue-penetrating medical tool, exposed for electrical contact with the subject's body and electrically-connected to an electrical power supply and an impedance meter for measuring the impedance between the first electrode and a second electrode in electrical contact with the subject's body; and a processor and display for analysing the ultrasound echoes and displaying an ultrasound image of the body and adapted to display on the ultrasound image the position of the tissue-penetrating medical tool as detected by the position detection system.

The invention also provides a corresponding method of obtaining and displaying an a medical image together with a tracked tissue penetrating tool and bio-electrical property measurement.

Thus with the invention the fact that the tissue-penetrating medical tool may have a low echogenecity is overcome by using magnetic position detection, in particular by magnetising the tool and using an array of magnetometers on the ultrasound transducer to detect the field from the magnetised tool. The magnetically detected position and/or track of the tool is then displayed in the ultrasound image. Furthermore, the tool is provided with an electrode at its insertion end, for example at or near the tip of the tool, which is exposed for electrical contact with the tissue being penetrated so that by use of an electrical power supply and impedance meter, the impedance between the electrode at the insertion end of the tool and a second electrode in contact with the subject can be measured. This gives an indication of the impedance of the tissue, and thus of the tissue type, at and around the insertion end of the tool.

Preferably the output of the impedance meter is connected to the processor and display so that the measured impedance can be displayed with the ultrasound image. The impedance values may be displayed as a number or more preferably as a chart showing the variation in impedance as the tool is inserted. The chart may be displayed alongside the ultrasound image, or more preferably overlaid on the ultrasound image along the displayed position or track of the tool. Alternatively, or in addition, a display attribute of the ultrasound image, especially along the position or track of the tool may be set in accordance with the measured impedance, for example it may be colour-coded or the greyscale value varied. This may provide a colour or other image-attribute overlay on the ultrasound image.

If the tissue penetrating medical tool is out of the imaging plane of the ultrasound transducer then the processor and display may be adapted to show a position of the tool projected into the ultrasound imaging plane. The fact that it is a projected position can be indicated by visually distinguishing it from an actual position, for example by showing it dotted or in a different colour.

It is known that different tissue types have different electrical impedances and it is possible, therefore, to determine the tissue type from the electrical impedance. Consequently the system may be adapted to determine the tissue type from the measured impedance value and then to colour-code areas of the ultrasound image using colour-coding typically used in medical anatomy texts.

The tissue-penetrating medical tool can be a needle, a catheter, a cannula or stylet and the electrode can be provided at or near the tip of the tool. The tool can, therefore, be a standard electrically-stimulating needle or catheter which has a built-in electrode at the distal, insertion end and electrical connections at the proximal end.

The second electrode may be provided for application to the subject's skin in which case the measured impedance is representative of the path or paths from the tip of the tissue-penetrating tool to the skin electrode. Multiple electrodes on the skin can also be used. On the other hand the second electrode may be provided on the tissue-penetrating tool itself, preferably at or near the tip but spaced and insulated from the first electrode so as to provide a measurement of the impedance of the tissue at or around the tip of the tool. Alternatively the second electrode may be provided on a second insertable instrument such as a second needle of narrower gauge which can be inserted down the lumen of a first needle, on a stylet for insertion into the lumen of the medical tool or on a catheter for insertion through the medical tool. The invention may, therefore, use one of the standard electrically-stimulating catheters which include a built-in electrode at their distal end.

The electrical power supply may be adapted to provide DC or AC power and at a selectable number or range of frequencies so that the tissue impedance can be measured with DC or at a range of frequencies. Alternatively the frequency may be scanned over a range, or time-domain pulses which are shaped to comprise plural frequency domain components can be applied to measure the response at plural frequencies simultaneously.

The position detection system is preferably one of: a magnetic position detection system, an optical tracking system, an electromagnetic tracking system or an ultrasonic tracking system. Electromagnetic systems based on installing sensors, e.g. coils, in the tissue-penetrating medical tool and applying a varying magnetic field in the detection space may be used. Such sensors detect the applied magnetic field and send a signal to a position determination system. X-ray based tracking systems may also be used.

More preferably the position detection system is a magnetic position detection system comprising an array of magnetometric sensors positioned on the ultrasound transducer for detecting the position of a magnetised tissue-penetrating medical tool relative to the ultrasound transducer. This has the advantage that the tissue-penetrating tool is a standard one which has been magnetised, and that a freehand ultrasound transducer may be used.

Another aspect of the invention provides an ultrasound image guided surgical method comprising the steps of: obtaining an ultrasound image from a subject's body while inserting a tissue-penetrating medical tool into the body; detecting the position of the tissue-penetrating medical tool and displaying the detected position on the ultrasound image; and measuring and displaying the electrical impedance measured between a first electrode provided at the insertion end of the tissue-penetrating medical tool and a second electrode in electrical contact with the subject's body.

The invention therefore makes available to the clinician the image information, the detected position information and bio-electrical e.g. impedance, data on the tissue being penetrated. The delivery and presentation to the clinician of these three sources of information make the surgical procedure much safer. Further, it achieves this without substantial modification of the instruments used by the clinician and thus without needing substantial modification of the surgical procedures.

The presence of the first electrode on the medical tool also allows electrical stimulation of the tissue or electrical treatment to be carried out. For example, by applying an electrical stimulus to nerves the nerve conduction can be measured to give an indication of the effectiveness of an anaesthetic block.

The impedance measurements can be used in combination with the ultrasound image to aid image processing of the ultrasound image. For example it is possible to use the impedance information, together with ultrasound information, to segment the displayed image into different tissue types.

The invention may be combined with the delivery of ultrasound contrast agents and the impedance measurements may be used, rather than detecting the subject's tissue, to detect objects (screws, plastic, surgical devices), materials (silicone etc.) or other tissue modifications inside the subject's body.

The invention will be further described by way of examples with reference to the accompanying drawings in which:—

FIG. 1 is a schematic diagram of a system according to one embodiment of the invention;

FIG. 2 (A) to (E) schematically illustrate different tissue-penetrating medical tools usable in the system of the invention;

FIG. 3 (A) to (E) illustrate different image displays according to embodiments of the invention;

FIG. 4 schematically illustrates a magnetometric detector according to one embodiment of the invention; and FIG. 5 schematically illustrates a base station for the magnetometric detector of FIG. 4.

As shown in FIG. 1 the system in this embodiment of the invention comprises an ultrasound imaging system 1 including an ultrasound transducer 2, processor 3 and display 4. The system also comprises a tissue-penetrating medical tool 5 such as a needle or cannula which is provided at its insertion end 6 with an electrode 7, the electrode 7 being connected to an impedance meter 8 and source of electrical power 9. To complete the electrical circuit through the subject's body 10 a second electrode 11 is provided in contact with the subject's body. In FIG. 1 the second electrode 11 is illustrated schematically as a skin-adhering electrode, though other possibilities for positioning the second electrode on the tool 5 will be discussed below. The impedance meter 8 and electrical power source 9 may be in a combined off-the-shelf impedance analyzer which has an onboard frequency generator which can excite complex impedance of the subject's tissue with a known frequency and which also analyses the response signal with a onboard digital signal processor that outputs as data the real and imaginary parts of the impedance.

An embodiment of the invention using magnetic position detection to track the tissue penetrating tool 5 will be described, though it will be appreciated that other tracking modalities can be used. Thus in this embodiment the tool 5 is magnetised and the ultrasound transducer 2 is provided with a magnetometric detector 12 comprising an array of magnetometers 120. The detector 12 senses the magnetic field from the tool 5, together with the earth's magnetic field and any other background magnetic field, and the processor 3 is adapted to determine from the detected field the position and orientation of the tool 5 relative to the transducer 2. This magnetically detected position is then displayed on the display 4 together with the ultrasound image.

The ultrasound system 1 can be a standard two dimensional B-mode ultrasound system with the standard ultrasound probe 2 being modified by the provision of the magnetometric detector 12. The processor 4, which is connected to the ultrasound probe via a cable, drives the ultrasound transducer 2 by sending electrical signals to cause it to generate ultrasound pulses and interpreting the raw data received from the transducer 2, which represents echoes from the subject's body, to assemble it into an image of the patient's tissue. The magnetometric detector 12 may be detachably attached to the ultrasound transducer 2 and can be battery-powered or powered from the ultrasound system. Preferably positioning elements are provided on the magnetometric detector 12 to ensure that it is always attached in the same well-defined position and orientation. The magnetometric detector 12 is connected by a wireless connection 15 to a base unit 14 which is in wireless or wired (e.g. USB) communication 16 with the ultrasound processor 3 and display 4. The base unit 14 can be integrated with, or some of its functions performed by, the ultrasound processor 3 or the magnetometric detector 12. As will be explained in more detail below, the base unit 14 receives normalised measurements from magnetometric detector 12 and calculates the position, or optionally the position and orientation, of the medical tool 5. The base unit 14 can also receive additional information such as the state of charge of the magnetometric detector's battery and information can be sent from the base unit 14 to the magnetometric detector 12, such as configuration information. The base unit 14 forwards the results of its calculations, i.e. the position and, optionally, orientation, to the ultrasound image processor 3 for inclusion in the displayed ultrasound image of an image 17 of the tool 5. This will be explained in more detail below.

As illustrated in FIG. 1, and in accordance with the invention, the system also measures the electrical impedance of the body tissue of the subject. Thus the tool 5 carries at its insertion end the first electrode 7 which is exposed to the subject's body tissue and is electrically connected via impedance meter 8 and power supply 9 to a second electrode 11 to complete a circuit with the subject's body. The tool 5 may, for example, be a standard electrical stimulating needle which includes a built-in electrode 7. The power supply 9 may, as schematically illustrated, apply either DC or AC and, if AC, applies a single frequency or a range of frequencies, or a frequency sweep. It is also possible for the power supply 9 to apply electrical pulses to give an instantaneous range of frequencies thus measuring the response at different frequencies simultaneously. The impedance meter 8 measures the impedance and digitises the value for transmission 13 to the ultrasound processor 3. The impedance analyzer components 8 and 9 are in practice preferably integrated into a single unit.

Although the use of the base station 14 and impedance analyzer components 8 and 9 separate from the ultrasound system 1 is advantageous in requiring less modification of the ultrasound system 1, it will be appreciated that any of these can be integrated into the ultrasound system 1 with the processor 3 taking-over the functions of the processor 180 and the control and analysis functions of the impedance analyzer components 8 and 9. The magnetometric detector 12 can then be in direct communication with the ultrasound system 1 either via wireless link or using the same physical cable as the ultrasound probe 2.

FIG. 1 schematically illustrates the tissue-penetrating medical tool as a standard nerve stimulating needle to be used in combination with a standard skin-adhering electrode 11. FIG. 2(A) shows the insertion end of the needle in more detail with the electrode 7 on the side of the needle at its tip. Alternative configurations are, however, possible as illustrated in FIG. 2(B) to (E). FIG. 2(B) illustrates a needle 5 in which the second electrode 11' is also positioned at or near the needle tip. As illustrated it is on the opposite side from the first electrode 7, though it can be positioned on the same side, spaced along the needle wall from the first electrode 7.

FIG. 2(C) illustrates an embodiment in which two standard stimulating needles of different gauges are used, one inside the other. Thus lumen of the needle 5 carrying the first electrode 7 is occupied by a second standard stimulating needle 50 which carries the second electrode 11' at its insertion end. This arrangement with two concentric needles allows the injection of liquids at the same time as impedance measurements.

FIG. 2(D) illustrates an embodiment in which the second electrode 11' is positioned on the insertion end of a standard electrically stimulating catheter 60 which is inserted down the lumen of the needle 5.

FIG. 2(E) illustrates an embodiment in which the second electrode 11' is positioned on the distal end of a stylet 70 passed down the lumen of the needle 5.

It is, of course, necessary that the electrodes 7 and 11' are insulated from the material of the tool 5 when the tool is electrically conductive. Further, in the concentric arrangements of FIGS. 2(C), (D), and (E) either the inside of the tool 5 or the outside of the inner needle, stylet or catheter can be electrically insulated.

The electrical connections to the power supply 9 and impedance meter 8 are preferably provided at the proximal end of the tool 5 in the same way as for a standard electrical stimulation needle or catheter.

It will be appreciated that whereas the embodiment of FIG. 2(A) measures the impedance along the path between the first electrode 7 and the skin electrode 11, the embodiments of FIGS. 2(B) to 2(E) measure the electrical impedance closely in the vicinity of the tip of the tool 5 by virtue of the first and second electrodes being positioned closed together in the tissue into which the tool is being inserted. The embodiment of FIG. 1 is therefore well-suited to detecting and indicating changes impedance as the tool is inserted, which may be sufficient to inform clinician performing the insertion procedure. In other words the clinician may simply be interested to note the changes in tissue type as the tool is inserted, without needing to know the absolute value of the impedance of the tissue at the tool tip. On the other hand the embodiments of FIGS. 2(B) to 2(E) can give an absolute measurement of the impedance of the tissue at the tool tip and this impedance value can be converted into a tissue type by referring to measured impedances of different tissue types, for example as found in: Herman et al, "Specific resistance of body tissues", Circulation Research, volume IV, November 1956.

Optionally where the impedance is measured at a range of frequencies it is possible to compress the different values into a single impedance metric value for display to the user.

The magnetometric detector 12 and the way in which the position of the magnetised tool 5 compared to the ultrasound probe 2 are calculated will now be explained in more detail. These techniques are described in our co-pending International (PCT) patent application PCT/EP2011/065420.

The components of the magnetometric detector 12 are shown schematically in greater detail in the block diagram of FIG. 4. The magnetometric detector 12 comprises an array 100 or two or more (e.g. four) magnetometers 120 (not shown in FIG. 4) whose outputs are sampled by a microprocessor 110. The microprocessor 110 normalizes the measurement results obtained from the magnetometer array 100 and forwards it to a transceiver 115 with an antenna 130 which, in turn transmits the information to the base unit 14. In a modified version of this embodiment, the magnetometric detector 12 is provided with a multiplexer rather than with a microprocessor 110 and the normalization is performed by a processor 180 in the base unit 14.

Each magnetometer 120 in the array 100 of magnetometers measures the components $a_k^u$, $a_k^v$, $a_k^w$ (k indicating the respective magnetometer) of the magnetic field at the position of the respective magnetometer 120 in three linearly independent directions. The microprocessor 110 transforms these raw values:

$$a_k = (a_k^u, a_k^v, a_k^w)$$

into corresponding normalized values:

$$b_k = (b_k^x, b_k^y, b_k^z)$$

in predetermined orthogonal directions of equal gain by multiplying the three values $a_k$ obtained from the magnetometer with a normalisation matrix $M_k$ and adding a normalisation offset vector $\beta_k$:

$$b_k = a_k * M_k + \beta_k$$

as will be described in more detail below. The normalisation matrices and the normalisation offset vectors are permanently stored in a memory associated with the microcontroller. This same transformation is performed for each of the magnetometers 120 with their respective normalisation matrix and adding a normalisation offset vector such that the result $b_k$, for each magnetometer provides the components of the magnetic field in the same orthogonal spatial directions with identical gain. Thus, in a homogenous magnetic field, all magnetometers always provide identical values after normalisation regardless of the strength or orientation of the homogenous magnetic field.

Normalisation and Offset

All magnetometers should measure equal values when exposed to a homogeneous field. For example, a magnetometer rotated in the homogeneous terrestrial magnetic field should, depending on the orientation of the magnetometer, measure varying strengths of the components of the magnetic field in the three linearly independent directions. The total strength of the field, however, should remain constant regardless of the magnetometer's orientation. Yet, in magnetometers available on the market, gains and offsets differ in each of the three directions. Moreover, the directions oftentimes are not orthogonal to each other. As described for example in U.S. Pat. No. 7,275,008 B2 for a single sensor, if a magnetometer is rotated in a homogeneous and constant magnetic field, the measurements will yield a tilted 3-dimensional ellipsoid. Because the measured field is constant, however, the normalized measurements should lie on a sphere. Preferably, an offset value $\beta$ and a gain matrix M are introduced to transform the ellipsoid into a sphere.

With a set of sensors, additional steps need to be taken to assure that the measurements of different sensors are identical with each other. To correct this, preferably, set of a gain normalisation matrices $M_k$ and normalisation offset vectors $\beta_k$ for each position k are determined which transform the magnetometer's raw results $a_k$ into a normalized result $b_k$:

$$b_k = a_k * M_k + \beta_k$$

Such a set of gain matrices $M_k$ can be obtained by known procedures, for example the iterative calibration scheme described in Dorveaux et. al., "On-the-field Calibration of an Array of Sensors", 2010 American Control Conference, Baltimore 2010.

By virtue of the defined transformation, $b_k$ provides the strength of the component of the magnetic field in three orthogonal spatial directions with equal gain. Moreover, it is ensured that these directions are the same for all magnetometers in the magnetometric detector. As a result, in any homogeneous magnetic field, all magnetometers yield essentially identical values.

The normalisation information $M_k$ and $\beta_k$ for each magnetometer as obtained in the calibration step can be stored either in the magnetometric detector 12 itself or in the base unit 14. Storing the information in the magnetometric detector 12 is preferred as this allows easy exchange of the magnetometric detector 12 without the need to update the information in the base unit. Thus, in a preferred embodiment of the invention, the outputs of the magnetometers of the magnetometric device are sampled and their results are normalised in the magnetometric detector 12. This information, possibly together with other relevant information, is transmitted to the base unit 14 for further analysis.

In another embodiment of the invention, the transformation can be another, more general non-linear transformation $b_k = F(a_k)$.

In addition to the above calibration method, another calibration method is applied which employs an inhomogeneous magnetic field to obtain the relative spatial locations of the magnetometric detector's magnetometers. While standard calibration methods utilize a homogenous magnetic field to (a) align the measurement axis of the magnetometers orthogonally, (b) cancel the offset values and (c) adjust to equal gain, it is of further advantage to the described systems that also the precise relative spatial locations of the magnetometers are available. This can be achieved by an additional calibration step in which the magnetometric detector is subjected to a known inhomogeneous magnetic field. Preferably, comparing the obtained measurements at the various positions to the expected field strengths and/or orientations in the assumed locations, and correcting the assumed locations until real measurements and expected measurements are in agreement, allows for the exact calibration of the spatial positions of the sensors.

In a variation of the latter calibration method, an unknown rather than a known homogeneous field is used. The magnetometers are swept through the unknown magnetic field at varying positions, with a fixed orientation. With one of the magnetometers supplying a reference track, the positions of the other magnetometers are adaptively varied in such a way that their measurements align with the measurements of the reference unit. This can be achieved for example by a feedback loop realizing a mechano-magnetic-electronical gradient-descent algorithm. The tracks used in this inhomogeneous field calibration can be composed of just a single point in space.

Model Fitting and Position Detection

The base station 14 shown schematically in greater detail in FIG. 5 receives the normalised positional information from the magnetometric detector 12 through its receiver 160 with antenna 170 and forwards the information to a processor 180. There, the normalized results of the measurements are combined to derive the position (or position and orientation) of the tool 5. For this purpose, the values $b_k$ are used to fit a model $c_k(p)$ of the combined magnetic field originating from the magnetic tool 5 and the terrestrial magnetic field. The unknown parameters p in this model are the tool's location I relative to the ultrasound transducer 2, it's length and orientation d and it's magnetic coercivity m as well as the terrestrial magnetic field E:

$$p = \{I, d, m, E\}$$

The model $c_k(p)$ comprises the normalized components $c_k^x(p)$, $c_k^y(p)$, $c_k^z(p)$ of the magnetic field at the position of magnetometer k at a given set of parameters p. By means of appropriate algorithms known to the skilled person the parameters p are obtained at which the deviation of the components of the magnetic field according to the model from the components actually measured is minimized:

$$\Sigma_k (b_k - c_k(p))^2$$

Suitable minimization techniques are for example gradient-descent algorithms as well as Levenberg-Marquardt approaches. Moreover, Kalman filter techniques or similar iterative means can be utilized to continuously perform such an operation.

If the tool 5 is sufficiently rigid, i.e. it bends only slightly, it can be approximated as a straight hollow cylinder. The magnetic field of such cylinder is equivalent to that of opposite magnetic charges (i.e. displaying opposite magnetic force) evenly distributed on the end surfaces of the cylinder, i.e. two circular rings at the opposite ends of the tools, the rings having opposite magnetic charge. In view of the small diameter of the tool 5, the charges can be further approximated by two magnetic point charges at the opposite ends of the tool 5. Thus, according to the model, the magnetic field of a tool 5 extending along the vector d is measured from a position $r_k$ is:

$$N(r_k, d, m) = m^* (r_k / |r_k|^3 - (r_k + d)/|r_k + d|^3).$$

Here $|r_k|$ and $|r_k + d|$ indicate the absolute values of the vectors $r_k$ and $r_k + d$, respectively. The positions $r_k$ can be converted to the location I of the tool 5 relative to the ultrasound transducer 2 with the help of the known positions of the magnetometers 120 in the magnetometric detector 12 and the position of the magnetometric detector 12 relatively to the ultrasound transducer 2. Consequently, further considering the terrestrial magnetic field E, the components of the magnetic field according to the model amount to:

$$c_k(p) = N(r_k, d, m) + E = m^* (r_k / |r_k|^3 - (r_k + d)/|r_k + d|^3) + E$$

Note that in contrast to many known approaches the above model does not assume the field of the needle to be a dipole field. This would be an oversimplification as the magnetometric detectors in general are too close to the needle as compared to the length of the needle to make a dipole field a valid approximation.

The needle position obtained by fitting the model to the measured magnetic field values $b_k$ detected by the magnetometers 120 as described above is then forwarded via link 16 to the processing unit 3. There, it is superimposed on the image of the tissue as obtained from the handheld ultrasound transducer 2.

If the tool 5 is in the imaging plane of the ultrasound transducer 2 the needle can be displayed as a solid line as illustrated schematically in FIG. 1. It is possible, however, that the needle is not in the ultrasound imaging plane. In such a case it is possible to display a position of the needle as projected onto the ultrasound image plane and to indicate in the display that it is a projected position by changing its display style. For example it can be displayed dotted and/or in a different colour. The tool is always visualised as a line, the end of which corresponds to the tool's tip. It is possible for the colour or display style to change depending upon whether the tool is in front of behind the imaging plane, and indeed if it cuts the imaging plane, parts behind can be displayed in one way and parts in front in another way.

It is also possible to display the whole expected needle track on the image display, this being a straight line extension of the tool's extent. Where anatomical features can be identified in the ultrasound image it is also possible to highlight the intersection of the needle track with these features, for example by displaying a circle or rectangle on the intersection.

Although in FIG. 1 the magnetometers 120 are displayed in an array across the front of the ultrasound transducer 2, it is also possible for them to be arranged in different ways on the ultrasound transducer 2.

Optionally the transducer 2 can also be provided with an inertial measurement unit which measures the position and orientation of the transducer by monitoring its acceleration from an initial position.

Magnetic Tool

The magnetic tool 5 is at least partly a permanent magnet, however the tool 5 may include a magnetic component which is a non-permanent magnet, e.g. an electromagnet, e.g. a solenoid to which an electric current can be applied to create the magnetic field. Alternatively the inserted part of the tool 5 may be magnetic due to magnetic induction from outside the body or from another part of the tool 5.

The magnetisation may be provided by a magnetic coating, preferably a permanent magnetic coating. For this purpose, it may for example comprise permanent magnetic particles, more preferably nanoparticles. A "nanoparticle" is a particle that in at least two spatial dimensions is equal to or smaller than 100 nm in size.

In one embodiment of the invention, tool has an essentially uniform magnetization. In another embodiment, the magnetization is non-uniform in at least one dimension, i.e. the magnetic moment varies in magnitude and/or direction as a function of the location on the tool, thereby creating a one- or more-dimensional magnetic pattern, e.g. similar to the pattern of a conventional magnetic strip (at least one-dimensional) or disk (two-dimensional) as it is used for the storage of information e.g. on credit cards. In a preferred embodiment of the invention, a one-dimensional magnetic pattern may be recorded along the length of the tool. Advantageously, such a pattern can be useful to identify the tool. Also, by marking certain parts of the tool with different magnetic codes, these parts can be distinguished. It is an achievable advantage of this embodiment of the invention that the position and/or orientation of the tool can be better determined, as individual parts of the tool can be identified and individually tracked with respect to their position and/or orientation. In particular, advantageously, a varying shape of the tool, for example a needle bending under pressure, can be tracked. Moreover, a deformed tool and/or its deformation or degree of deformation can be determined more easily.

Display of Impedance

FIG. 3(A) to (E) illustrate different ways in which the impedance value measured by the impedance meter 8 can be displayed by the display 4. Of course the impedance value, or values as the tool 5 is inserted, can be displayed on a different display, for example associated with the impedance meter 8 itself, but advantageously they are displayed with the ultrasound image 4. Again, they may be displayed as simple numerical values, but it is particularly effective if they are displayed graphically aligned with the display 4 or over the position or track of the tool 5. FIG. 3(A), therefore, illustrates the impedance value being displayed as a chart along the tool path, trajectory. It can be seen that although the impedance values vary continuously along the path, there are larger step-like changes associated with the tip of the tool crossing tissue boundaries visible in the ultrasound image. These step-like changes therefore act as confirmations that the tool tip is crossing these different tissue types.

Figure 1:
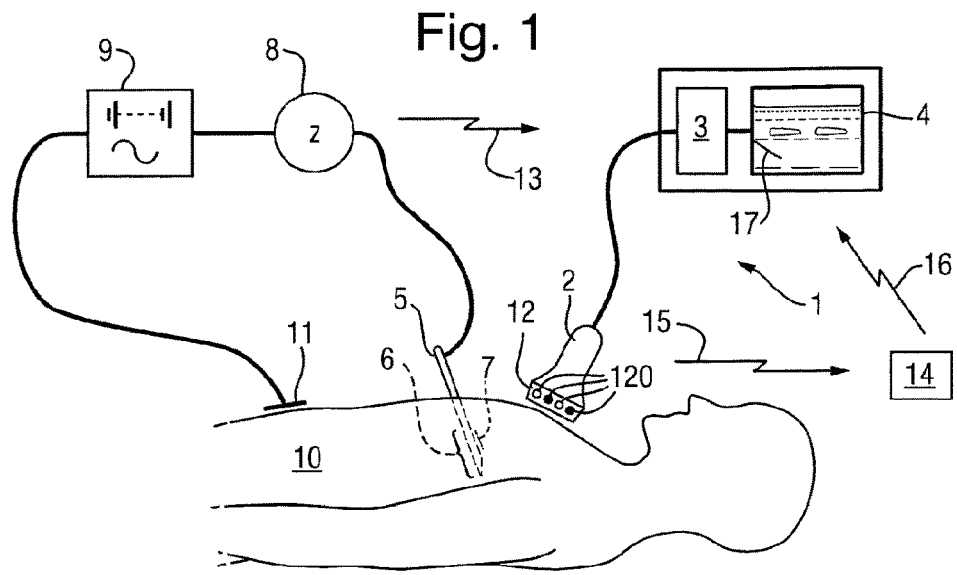
Figure 2A:
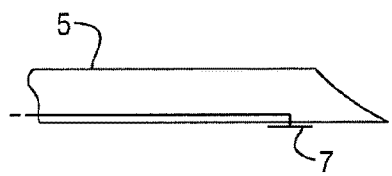
Figure 2B:
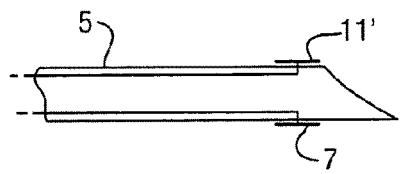
Figure 2C:
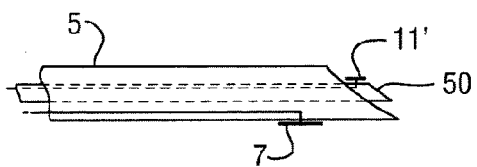
Figure 2D:
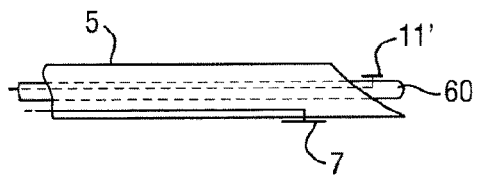
Figure 2E:
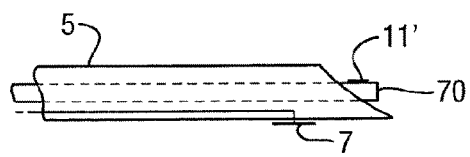
Figure 3E:
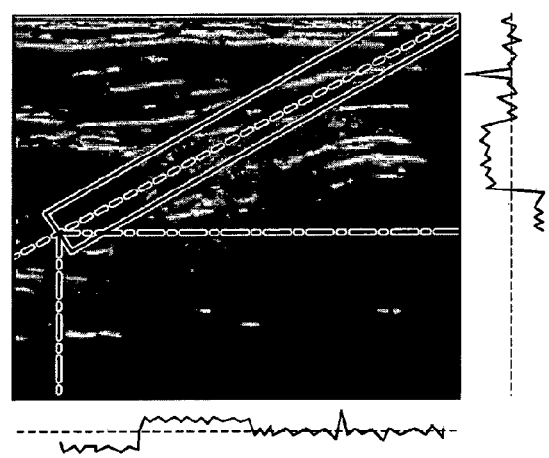
FIG. 3(B) illustrates the measured impedance values colour-coded and displayed as an overlay on the tool position/trajectory, and again colour changes can be seen to align with the tissue boundaries visible in the ultrasound image itself.
FIG. 3(C) illustrates the conversion of the impedance values to tissue type and overlaying on the ultrasound image a colour-coding based on the colour-coding from standard medical anatomy texts in which, for example, nerves are yellow, arteries red, bone is white.
FIG. 3(D) illustrates a variation on FIGS. 3(B) and 3(C) in which the colour-coding is only displayed at the position of the tool tip.
Figure 4:
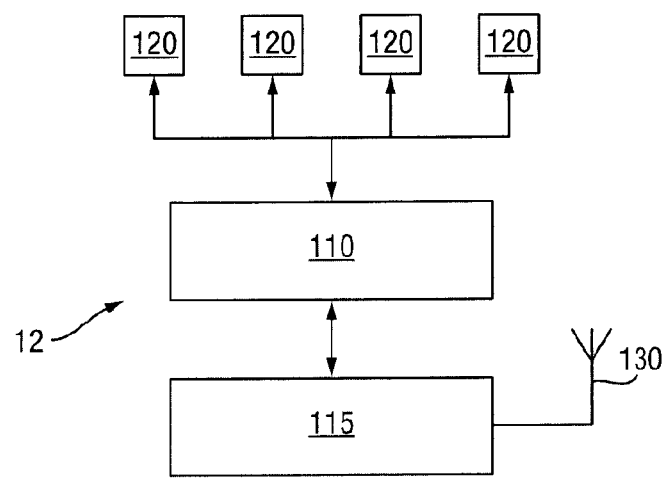
Figure 5:
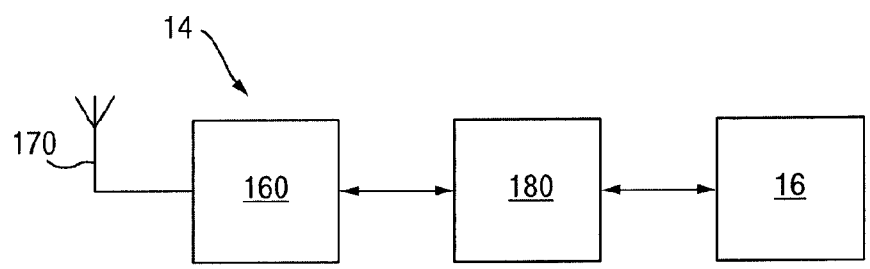

Rather than displaying the impedance value overlaid on the ultrasound image, it is also possible, as illustrated in FIG. 3(E) to display the impedance values either colour-coded or charted alongside the ultrasound image. As indicated in FIG. 3(E) to assist interpretation it is advantageous if the values are displayed along two orthogonal sides of the ultrasound image to allow the user to see the visual alignment between tissue boundaries in the ultrasound image and large changes in impedance value. The charted or colour-coded values are displayed in line with the position of the tip of the tool 5 projected onto the orthogonal sides of the image display.

While FIGS. 3(B), (C), and (D) illustrate the superimposition of transparent colour over the ultrasound image, it is alternatively possible to use different image attributes to indicate the impedance value. For example the greyscale value, or a single coloured greyscale scheme (i.e. ranging from black to the single colour of interest, e.g. red, over 256 different values) can be used.

Example Procedures

One procedure which can be assisted by the systems of the invention is that of delivering an epidural anaesthetic. Using the ultrasound imaging system the clinician can see bones in the spinal column and muscle and (sometimes) the dura in the ultrasound image. The magnetometric needle tracking allows the clinician to see the progress of the needle so that the needle tip can be brought quickly and easily close to the dura. The displayed impedance value gives the clinician confirmation of when the needle breaks the dura and enters the epidural space and confirmation that the needle has not advanced too far.

As another example, in a regional anaesthesia procedure the ultrasound and magnetometric needle tracking can be used in combination to bring the needle tip close to the nerve. The impedance value allows the clinician to confirm whether or not the tip of the needle is touching or inside the nerve before any anaesthetic is injected. The impedance value also indicates whether the needle has punctured a blood vessel and it will indicate whether the needle has passed through facia compartments surrounding nerves— the failure to do so is a common reason for the failure of many femoral nerve blocks.

In a needle aspiration procedure the impedance value can indicate to the user whether or not the needle is inside or outside a tumour thus allowing greater accuracy in the collecting of material.

The invention is also useful for training purposes as the colour-coding of tissue at the tip of the needle according to the impedance measurement and thus tissue type, allows less experienced users clear indications linking what they are seeing on the ultrasound image to the anatomy of the patient.

Although the electrode on the tool 5 primarily provided for the impedance measurement, it is also possible to use it to supply electrical stimulation. For example it is possible to measure nerve conduction by applying an electrical signal to the electrode 7 while it is in contact or close to a nerve. If the nerve is blocked properly (i.e. the anaesthetic has had the desired effect) the patient will not feel any sensation.

The invention claimed is:

1. A system comprising:
    an ultrasound transducer for transmitting ultrasound into a subject's body and receiving ultrasound echoes from the body;
    a tissue-penetrating medical tool having an insertion end for insertion into the body of the subject, wherein the tissue-penetrating medical tool comprises a needle or cannula that is magnetized;
    a magnetic position detection system for tracking the position of the magnetized tissue-penetrating medical tool in the body of the subject, wherein the position detection system comprises an array of magnetometric sensors positioned on the ultrasound transducer for detecting the magnetic field originating from the magnetized tissue-penetrating medical tool and adapted to calculate the position of the magnetized tissue-penetrating medical tool in the body of the subject relative to the ultrasound transducer;
    a first electrode provided at the insertion end of the magnetized tissue-penetrating medical tool, exposed for electrical contact with the subject's body and electrically-connected to an electrical power supply and an impedance meter for measuring the impedance between the first electrode and a second electrode in electrical contact with the subject's body; and
    a processor and display for analysing the ultrasound echoes and displaying an ultrasound image of the body and adapted to display on the ultrasound image the position of the magnetized tissue-penetrating medical tool as detected by the position detection system;
    wherein the impedance meter is connected to the processor and display to display the measured impedance with the ultrasound image on the display; and
    wherein the second electrode is positioned at or near the insertion end of the magnetized tissue-penetrating medical tool.

2. A system according to claim 1 wherein the processor and display are adapted to display a chart of the measured impedance over the display of the position of the magnetized tissue-penetrating medical tool in the ultrasound image.

3. A system according to claim 1 wherein the processor and display are adapted to display the measured impedance by setting a display attribute in the ultrasound image according to the measured impedance value.

4. A system according to claim 3 wherein the processor and display are adapted to set display attributes along the displayed position of the magnetized tissue-penetrating medical tool in the ultrasound image according to the measured impedance value.

5. A system according to claim 3 wherein the processor and display are adapted to set display attributes at the displayed position of the insertion end of the magnetized tissue-penetrating medical tool in the ultrasound image according to the measured impedance value.

6. A system according to claim 4 wherein the processor and display are adapted to set display attributes at a projected displayed position if the magnetized tissue-penetrating medical tool is out of the ultrasound image plane.

7. A system according to claim 3 wherein the display attribute set is the colour or grayscale value.

8. A system according to claim 7 wherein the processor is adapted to determine a tissue type from the impedance value and to display the ultrasound image with areas colour coded according to tissue type using standard medical anatomy colour coding.

9. A system according to claim 1 wherein the processor and display are adapted to display a chart of the measured impedance alongside ultrasound image.

10. A system according to claim 1 wherein the processor and display are adapted to display the change of impedance as the magnetized tissue-penetrating medical tool is moved through the subject's body.

11. A system according to claim 1 wherein the magnetized tissue-penetrating medical tool is a needle.

12. A system according to claim 1 wherein the first electrode is provided at the tip of the magnetized tissue-penetrating medical tool.

13. A system according claim 1 wherein the second electrode is provided on the insertion end of the needle or cannula spaced from the first electrode.

14. A system according to claim 1 wherein a plurality of second electrodes are provided.

15. A system according to claim 1 wherein the electrical power supply is adapted to supply power over a range of AC frequencies and the impedance meter is adapted to measure the impedance at a plurality of frequencies.

16. A system comprising:
    an ultrasound transducer for transmitting ultrasound into a subject's body and receiving ultrasound echoes from the body;
    a tissue-penetrating medical tool having an insertion end for insertion into the body of the subject, wherein the tissue-penetrating medical tool comprises a needle or cannula that is magnetized;
    a magnetic position detection system for tracking the position of the magnetized tissue-penetrating medical tool in the body of the subject, wherein the position detection system comprises an array of magnetometric sensors positioned on the ultrasound transducer for detecting the magnetic field originating from the magnetized tissue-penetrating medical tool and adapted to calculate the position of the magnetized tissue-penetrating medical tool in the body of the subject relative to the ultrasound transducer;
    a first electrode provided at the insertion end of the magnetized tissue-penetrating medical tool, exposed for electrical contact with the subject's body and electrically-connected to an electrical power supply and an impedance meter for measuring the impedance between the first electrode and a second electrode in electrical contact with the subject's body; and
    a processor and display for analysing the ultrasound echoes and displaying an ultrasound image of the body and adapted to display on the ultrasound image the position of the magnetized tissue-penetrating medical tool as detected by the position detection system;
    wherein the impedance meter is connected to the processor and display to display the measured impedance with the ultrasound image on the display;
    wherein the second electrode is positioned at or near the insertion end of the magnetized tissue-penetrating medical tool;
    wherein the magnetized tissue-penetrating medical tool comprises a stimulating catheter and the second electrode is provided on the stimulating catheter for insertion through the needle or cannula; and
    wherein the magnetized tissue-penetrating medical tool comprises a stimulating catheter and the second electrode is provided on the stimulating catheter for insertion through the needle or cannula.

17. A system comprising:
an ultrasound transducer for transmitting ultrasound into a subject's body and receiving ultrasound echoes from the body;
a tissue-penetrating medical tool having an insertion end for insertion into the body of the subject, wherein the tissue-penetrating medical tool comprises a needle or cannula that is magnetized;
a magnetic position detection system for tracking the position of the magnetized tissue-penetrating medical tool in the body of the subject, wherein the position detection system comprises an array of magnetometric sensors positioned on the ultrasound transducer for detecting the magnetic field originating from the magnetized tissue-penetrating medical tool and adapted to calculate the position of the magnetized tissue-penetrating medical tool in the body of the subject relative to the ultrasound transducer;
a first electrode provided at the insertion end of the magnetized tissue-penetrating medical tool, exposed for electrical contact with the subject's body and electrically-connected to an electrical power supply and an impedance meter for measuring the impedance between the first electrode and a second electrode in electrical contact with the subject's body; and
a processor and display for analysing the ultrasound echoes and displaying an ultrasound image of the body and adapted to display on the ultrasound image the position of the magnetized tissue-penetrating medical tool as detected by the position detection system;
wherein the impedance meter is connected to the processor and display to display the measured impedance with the ultrasound image on the display;
wherein the second electrode is positioned at or near the insertion end of the magnetized tissue-penetrating medical tool;
wherein the magnetized tissue-penetrating medical tool comprises a stimulating catheter and the second electrode is provided on the stimulating catheter for insertion through the needle or cannula; and
wherein the magnetized tissue-penetrating medical tool comprises a second needle, of different gauge, such as a stylet, for insertion into the needle or cannula, the second electrode being provided on the second needle.

* * * * *